(12) United States Patent
Ouchi et al.

(10) Patent No.: US 8,835,853 B2
(45) Date of Patent: Sep. 16, 2014

(54) PHOTOCONDUCTIVE ELEMENT

(75) Inventors: Toshihiko Ouchi, Machida (JP); Kousuke Kajiki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 173 days.

(21) Appl. No.: 13/416,447

(22) Filed: Mar. 9, 2012

(65) Prior Publication Data

US 2012/0235040 A1    Sep. 20, 2012

(30) Foreign Application Priority Data

Mar. 18, 2011   (JP) ................. 2011-061439

(51) Int. Cl.
*G01N 21/35* (2014.01)
*H01L 31/09* (2006.01)
*G01J 3/42* (2006.01)

(52) U.S. Cl.
CPC . *G01J 3/42* (2013.01); *H01L 31/09* (2013.01); *G01N 21/3586* (2013.01)
USPC ........................................... 250/341.1

(58) Field of Classification Search
CPC .............. G01N 21/3586; G01N 21/3581
USPC ........................................... 250/341.1
See application file for complete search history.

(56) References Cited

U.S. PATENT DOCUMENTS

| | | | |
|---|---|---|---|
| 4,551,394 A * | 11/1985 | Betsch et al. | 428/641 |
| 4,829,346 A * | 5/1989 | Kasahara et al. | 257/184 |
| 4,963,949 A * | 10/1990 | Wanlass et al. | 257/190 |
| 5,701,325 A | 12/1997 | Ouchi et al. | 372/96 |
| 6,046,096 A | 4/2000 | Ouchi | 438/510 |
| 6,222,868 B1 | 4/2001 | Ouchi et al. | 372/50 |
| 6,477,286 B1 | 11/2002 | Ouchi | 385/14 |
| 6,507,594 B1 | 1/2003 | Furukawa et al. | 372/36 |
| 6,836,579 B2 | 12/2004 | Ouchi | 385/14 |
| 7,615,787 B2 | 11/2009 | Ouchi | 257/76 |
| 7,633,043 B2 | 12/2009 | Ouchi | 250/214.1 |
| 7,693,198 B2 | 4/2010 | Sekiguchi et al. | 372/45.01 |
| 7,723,708 B2 | 5/2010 | Ouchi et al. | 250/493.1 |
| 7,839,910 B2 | 11/2010 | Asada et al. | 372/45.01 |
| 2003/0127673 A1 * | 7/2003 | Williamson et al. | 257/293 |
| 2006/0134892 A1 | 6/2006 | Evans et al. | 438/483 |
| 2007/0218376 A1 * | 9/2007 | Ouchi | 430/56 |

FOREIGN PATENT DOCUMENTS

JP     2006-086227     3/2006

OTHER PUBLICATIONS

O. Madelung (ed.), *Semiconductors—Basic Data*, 2$^{nd}$ rev. ed., pp. 78, 104 and 151 (Berlin, Heidelberg 1999).
H. Komatsu (ed.), *Handbook of Crystal Growth*, p. 699 (Kyoritsu Shuppan, 1995), with translation.

(Continued)

*Primary Examiner* — Constantine Hannaher
(74) *Attorney, Agent, or Firm* — Fitzpatrick, Cella, Harper & Scinto (57) ABSTRACT

Provided is a photoconductive element which solves a problem inherent in an element for generating/detecting a terahertz wave by photoexcitation that terahertz wave generation efficiency is limited by distortions and defects of a low temperature grown semiconductor. The photoconductive element includes: a semiconductor substrate; a semiconductor low temperature growth layer; and a semiconductor layer, which is positioned between the semiconductor low temperature growth layer and the semiconductor substrate and is thinner than the semiconductor low temperature growth layer, in which the semiconductor low temperature growth layer includes a semiconductor which lattice-matches with the semiconductor layer and does not lattice-match with the semiconductor substrate.

14 Claims, 6 Drawing Sheets

(56) References Cited

OTHER PUBLICATIONS

S. Gupta et al., "Ultrafast Carrier Dynamics in III-V Semiconductors Grown by Molecular-Beam Epitaxy at Very Low Substrate Temperatures", *IEEE Journal of Quantum Electronics*, vol. 28, No. 10, pp. 2464-2472 (1992).

B. Sartorius et al., "All-Fiber Terahertz Time-Domain Spectrometer Operating at 1.5 μm Telecom Wavelengths", *Optics Express*, vol. 16, No. 13, pp. 9565-9570 (2008).

R. Takahashi et al., "Ultrafast 1.55-μm Photoresponses in Low-Temperature-Grown InGaAs/InAlAs Quantum Wells", *Applied Physics Letters*, vol. 65, No. 14, pp. 1790-1792 (1994).

M. Tani et al., "Detection of Terahertz Radiation with Low-Temperature-Grown GaAs-Bbased Photoconductive Antenna Using 1.55 μm Probe", *Applied Physics Letters*, vol. 77, No. 9, pp. 1396-1398 (2000).

D-H Youn et al., "Structural Change and Its Electrooptical Effects on Terahertz Radiation with Post-Growth Annealing of Low-Temperature-Grown GaAs", *Japanese Journal of Applied Physics*, vol. 46, No. 10A, pp. 6514-6518 (2007).

\* cited by examiner

PHOTOCONDUCTIVE ELEMENT

BACKGROUND OF THE INVENTION

1. Field of the Invention

The present invention relates to a photoconductive element, as exemplified by an element for generating/detecting (which means an element capable of at least one of generation and detection) an electromagnetic wave in a frequency region from millimeter wavebands to terahertz wavebands (30 GHz to 30 THz). More specifically, the present invention relates to an optical semiconductor element for generating/detecting an electromagnetic wave pulse containing a Fourier component in the frequency region by optical pulse irradiation, and to a terahertz time domain spectroscopy apparatus using the optical semiconductor element.

2. Description of the Related Art

In recent years, non-destructive sensing technology using an electromagnetic wave ranging from millimeter waves to terahertz (THz) waves (30 GHz to 30 THz; hereinafter, also referred to simply as terahertz wave) has been developed. In the application field of the electromagnetic wave in this frequency band, imaging technology for safer fluoroscopy has been developed as an alternative to X-ray imaging. Other developing technologies include spectroscopic technology for determining absorption spectrum or complex permittivity inside a substance to examine physical properties such as the bonding state of molecules, measurement technology for examining physical properties such as the carrier density or mobility and the conductivity, and analysis technology for biomolecules.

A photoconductive element has been widely used for generating/detecting a terahertz wave. The photoconductive element includes a particular kind of semiconductor having relatively high mobility and sub-picosecond carrier lifetime, and two electrodes provided thereon. The photoconductive element is structured in a manner that, when a gap between the electrodes is irradiated with ultrashort-pulsed laser light under the application of voltage between the electrodes, a current flows between the electrodes instantaneously by excited photocarriers, and thereby a terahertz wave is emitted therefrom. The above-mentioned measurement and imaging technologies have been studied with the use of such photoconductive element also as a terahertz wave detector to constitute a terahertz time domain spectrosope device (THz-TDS).

In general, a titanium sapphire laser is used as an ultrashort-pulsed laser for excitation. There is, however, a demand for the use of a fiber laser at a telecommunication wavelength for reduction in size and cost. Since the wavelength in this case is 1 μm or more, low temperature grown (LT-)GaAs, which has heretofore been used as a photoconductive element, becomes a transparent medium and it cannot be used. LT-InGaAs is therefore being studied as an alternative photoconductive material (see Japanese Patent Application Laid-Open No. 2006-086227 and U.S. Patent Application Publication No. 2006/0134892).

However, since an InGaAs system has a smaller band gap than that of GaAs, the carrier density of an intrinsic semiconductor is higher, and in addition the number of crystal defects is apt to increase because InGaAs is ternary. Also owing to the increased residual carrier density, it is difficult to increase the resistance. Therefore, the application voltage cannot be increased as compared to GaAs and it is difficult to increase the differential change of photocarriers, which limits terahertz wave generation efficiency. The use of an InGaAs system as a detector increases a dark current to increase noise, which leads S/N ratio degradation. As countermeasures, another technology of using a semiconductor heterostructure as a photoconductive layer so as to trap generated carriers to thereby increase the resistance is being considered (see Optics Express, vol. 16, p. 9565 (2008)).

In the semiconductor heterostructure element described in Optics Express, vol. 16, p. 9565 (2008), however, a heterointerface deteriorates when a low temperature grown film is exposed to high temperature, and it is difficult to increase the carrier trapping effect as designed. Japanese Patent Application Laid-Open No. 2006-086227 also describes that the In composition is adjusted to be smaller than that of a lattice-matched system (0.45). With such value, the band gap is widened and the increase in resistance can be expected, but the degree of lattice mismatch with a substrate becomes larger. If the thickness is reduced in order to suppress lattice defects, the absorption amount of excited light is reduced and the amplitude of the terahertz wave is reduced.

SUMMARY OF THE INVENTION

It is therefore an object of the present invention to provide a structure for improving terahertz wave generation efficiency as well as the S/N ratio with the use of a low temperature growth layer.

In order to attain the above-mentioned object, the present invention provides a photoconductive element, including: a semiconductor substrate; a semiconductor low temperature growth layer; and a semiconductor layer, which is positioned between the semiconductor low temperature growth layer and the semiconductor substrate and which is thinner than the semiconductor low temperature growth layer. The semiconductor low temperature growth layer includes a semiconductor which lattice-matches with the semiconductor layer and does not lattice-match with the semiconductor substrate.

The present invention also provides a photoconductive element, including: a semiconductor substrate; a semiconductor low temperature growth layer; and a semiconductor layer, which is positioned between the semiconductor low temperature growth layer and the semiconductor substrate and which is thinner than the semiconductor low temperature growth layer. The semiconductor layer includes at least a first semiconductor region and a second semiconductor region. The first semiconductor region includes a semiconductor which lattice-matches with the semiconductor low temperature growth layer. The second semiconductor region includes a semiconductor which lattice-matches with the semiconductor substrate.

According to the present invention, the characteristics of the semiconductor low temperature growth layer can be improved to thereby generate a terahertz wave pulse efficiently by photoexcitation. Further, the S/N ratio can be improved. In particular, as necessary, a terahertz wave generating/detecting element which is effective for excited laser light at a telecommunication wavelength of 1 μm or more, and a measurement device and an imaging device which use the terahertz wave generating/detecting element can be provided. Besides, since an excited laser light source using a fiber can be used, the device can be reduced in size and cost.

Further features of the present invention will become apparent from the following description of exemplary embodiments with reference to the attached drawings.

DESCRIPTION OF THE EMBODIMENTS

Referring to the drawings, embodiments and examples of the present invention are described.

(First Embodiment)

Figure 1:
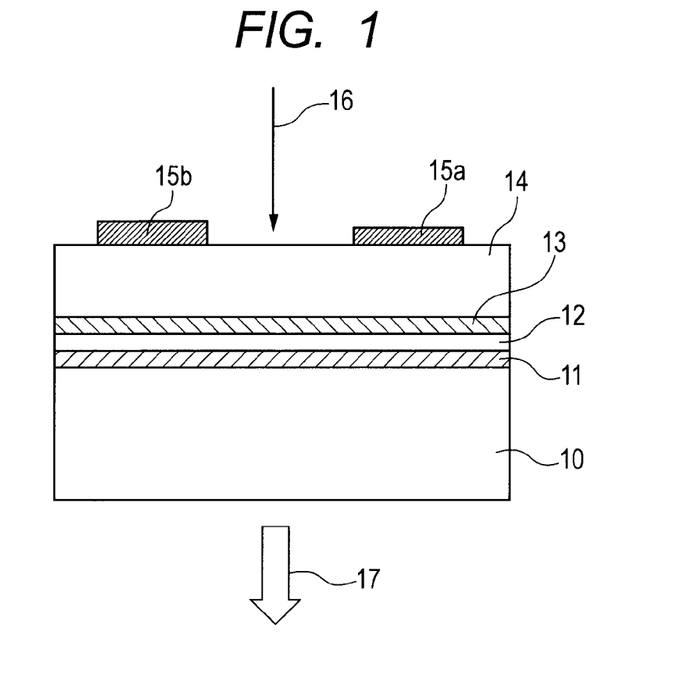
FIG. 1 is a cross-sectional structural diagram of a photoconductive element according to a first embodiment of the present invention.

Referring to FIG. 1, a first embodiment of the present invention is described. In this embodiment, an InGaAs layer 11, an InAlAs layer 12, and an InGaAs layer 13 are formed on a semi-insulating InP substrate 10 at a normal growth temperature, and an LT-InGaAs layer 14 is formed thereon by low temperature growth as a semiconductor low temperature growth layer. In order to function as a photoconductive element, a pair of electrodes 15a and 15b also serving as an antenna is formed on the surface.

The semiconductor low temperature growth layer 14 generates a terahertz wave 17 by irradiation of laser light 16. In order to operate with light at a wavelength of, for example, 1.55 μm and to increase the resistance, the semiconductor low temperature growth layer 14 is doped with Be at $10^{18}$ cm$^{-3}$ and grown at a growth temperature of 200° C. and further annealed at about 600° C. to enhance the crystallinity. The growth temperature of the semiconductor low temperature growth layer is 200° C. or more and less than 400° C., preferably 200° C. or more and 300° C. or less. The normal growth temperature as used herein refers to 400° C. or more and 700° C. or less, preferably 550° C. or more and 650° C. or less, typically about 600° C. For crystal growth, MBE growth or MOCVD growth can be used. The layers 11 to 13 are grown at a normal growth temperature so as to have relatively good crystallinity, and the growth is temporarily suspended in the same chamber. After the substrate temperature is decreased, low temperature growth is performed. As described above, the low temperature growth refers generally to growth at about 200° C. to about 400° C. in the same growth apparatus as that used for normal growth. It is known that generally the low temperature growth can shorten the carrier lifetime.

A semiconductor low temperature growth layer is widely used as an element for generating/detecting a terahertz wave because of the following effects. The use of a semiconductor low temperature growth layer having a short carrier lifetime as an element for generating a terahertz wave has an effect of reducing a residual carrier in the semiconductor low temperature growth layer to improve terahertz wave generation efficiency. The use of such semiconductor low temperature growth layer as an element for detecting a terahertz wave has effects of giving high-speed response and reducing dark current. In general, the extent of the carrier lifetime is desired to be sub-nanoseconds. A measurement example in which such a value is realized at a growth temperature of less than about 400° C. is known (APL, vol. 65, p. 1790). The low temperature growth is apt to be an unstable process because the crystallinity deteriorates. It is therefore more desired to set the growth temperature to 300° C. or less. The above-mentioned numerical example is intended for LT-InGaAs, but the same conditions apply to LT-GaAs, for example. Another known feature of the low temperature growth is, for example, that the content of As becomes larger than the stoichiometric composition by about 1% (IEEE Journal of quantum electronics, vol. 28, p. 2464).

As described above, the semiconductor low temperature growth layer is subjected to annealing after the growth in order to increase the resistance and improve the crystallinity. Arsenic (As) crystals in the semiconductor low temperature growth layer are clustered (to be several nm or more) by annealing. According to X-ray measurement data (JJAP, vol. 46, 6514), which is a generally known example of TEM observation, a low temperature grown GaAs layer has the properties of low peak intensity, wide peak linewidth, and peak angle deviation as compared with a GaAs substrate. Low peak intensity and wide peak linewidth mean low crystallinity of the semiconductor low temperature growth layer. Peak angle deviation means the change in lattice constant. Based on the above-mentioned features of the low temperature growth layer, the semiconductor low temperature growth layer can be discriminated from a layer which is grown at a normal growth temperature (having good crystallinity, low etch pit density (EPD), low excess As content, and no As clusters).

The annealing may be performed in the same chamber after the finish of growth, may be performed in another heating furnace after the substrate is taken out from the chamber, or may be performed in combination. In any case, in order to prevent scattering of As during heating, it is desired to raise a partial pressure of As by irradiation of As molecules, for example.

The thickness and function of each layer are as follows. The InGaAs layer 11 is an undoped layer having a thickness of about 100 nm to about 1,000 nm and it has a function of retaining a semiconductor low temperature growth layer having relatively weak strength. The undoped InAlAs layer 12 thereon has a thickness of about several tens of nm and forms a heterointerface with the InGaAs layer 11 to function as a carrier blocking layer, thereby preventing the lowering of the resistance. The undoped InGaAs layer 13 has a thickness of several nm and it is a cover layer for preventing the InAlAs layer 12 from being oxidized during the suspension of growth for decreasing the substrate temperature. The LT-InGaAs layer 14 is doped with Be for defect compensation as described above, the thickness of which desirably corresponds to about the absorption length of the irradiated laser light 16, typically about 1.6 μm. As described here, the semiconductor growth layers 11 to 13, which are grown at a normal growth temperature, include the semiconductor layer 12 having a band gap wider than that of the semiconductor low temperature growth layer 14.

Conventionally, if there is no layer grown at a normal growth temperature, layers having a large number of defects are concentrated at the interface with an InP substrate, and hence it has been difficult to increase the resistivity. In this embodiment, the defect density in the vicinity of the interface can be reduced to improve the resistivity. As a result, in a photoconductive element configured to generate the terahertz wave 17 in transmission arrangement through irradiation of the excited laser light 16, a higher voltage can be applied between the electrodes 15a and 15b. This increases the transfer rate of photocarriers excited in the low temperature growth layer, thus increasing the amplitude of a generated terahertz wave. Such photoconductive element can be used as a terahertz wave detector similarly to a normal photoconductive element.

Despite that the InGaAs/InAlAs/InP system is exemplified in this embodiment, the present invention is also applicable to compound semiconductors such as GaAs/AlGaAs/GaAs, InGaAs/AlGaAs/GaAs, InGaAsP/InP, GaAsSb/InP, GaAsSb/GaAs, InGaSb/GaSb, and InGaAlP/GaAs. The mole fraction and the growth substrate can be selected depending on excited laser light to be used. An example of an effective combination for excited laser light at a telecommunication wavelength includes an element that uses an $In_xGa_{1-x}As$ ($0 \leq x \leq 1$) layer or a $GaAs_ySb_{1-y}$ ($0 \leq y \leq 1$) layer as the semiconductor low temperature growth layer and uses a GaAs or InP substrate. Alternatively, compound semiconductor growth may be performed with the use of a Si substrate and a buffer layer interposed therein.

EXAMPLE 1

In Example 1 of the first embodiment, a layer that lattice-matches with an InP substrate (lattice constant: about 0.587 nm) is used. From a practical viewpoint of the element, a lattice-matched layer as used herein refers to a layer whose thickness does not exceed a critical thickness even if grown to be about several hundreds of nm or more in thickness, specifically, a layer which has the degree of lattice mismatch of 0.1% or less (see, for example, H. Komatsu ed., Handbook of Crystal Growth, Kyoritsu Shuppan, p. 699, 1995), and a lattice-mismatched layer refers to a layer which has a larger degree of lattice mismatch than 0.1%. In view of the above, the InGaAs layer 11, the InAlAs layer 12, and the InGaAs layer 13 were set to have In compositions of 0.53, 0.52, and 0.53 and thicknesses of 270 nm, 20 nm, and 5 nm, respectively. The semiconductor low temperature growth layer 14 was set to have an In composition of 0.53 and a thickness of 1.6 μm.

Figure 6:
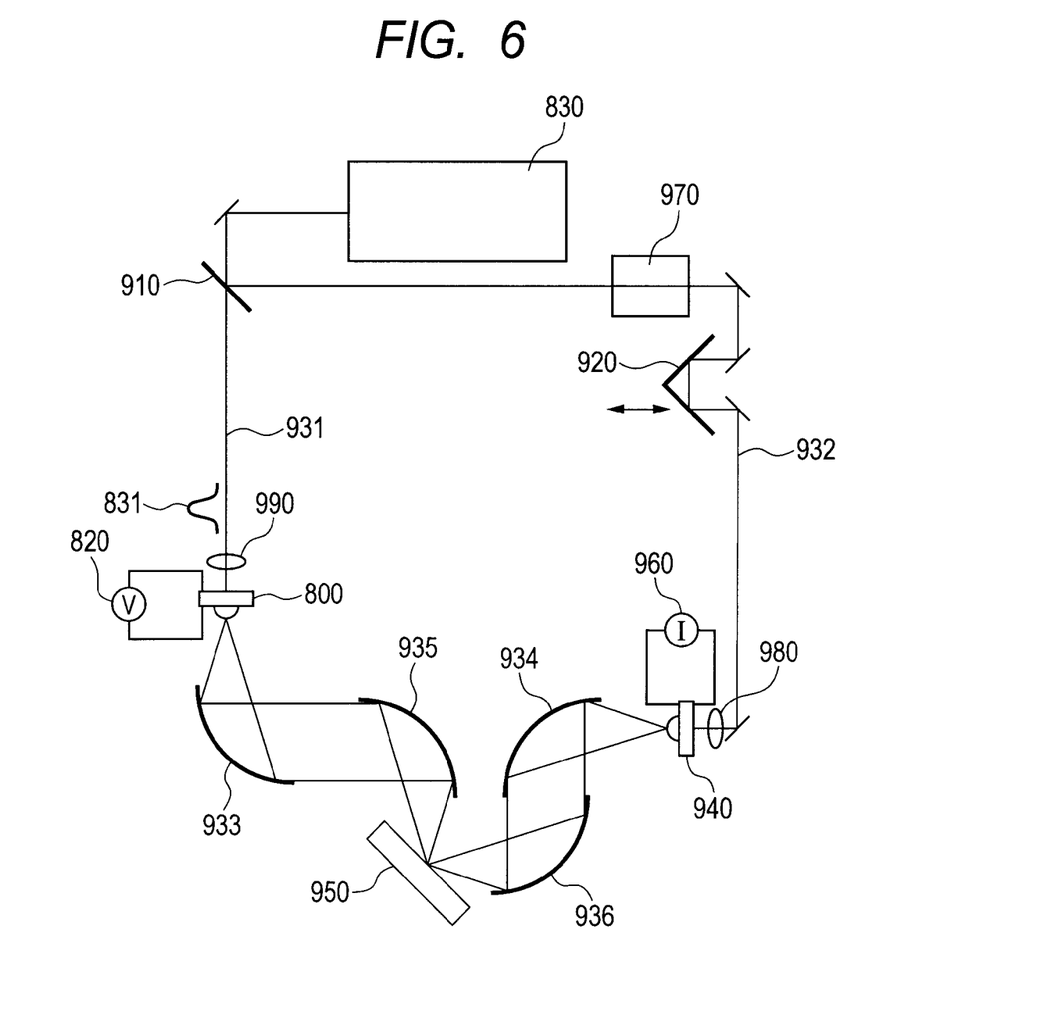
FIG. 6 is a configuration diagram of a terahertz wave generating device and a spectroscopy apparatus using the terahertz wave generating device according to the present invention.

An example of configuring a time domain spectroscopy apparatus by using the element of this example as a terahertz wave pulse generating element is as follows. FIG. 6 illustrates a terahertz time domain spectroscope system (THz-TDS) according to this example. The spectroscope system itself is basically identical with a conventionally-known spectroscope system and it is therefore described briefly.

The spectroscope system includes as main components a short-pulsed laser 830, a half mirror 910, an optical delay system 920, an electromagnetic wave generating element 800, and an electromagnetic wave detection element 940. Pump light 931 (ultrashort-pulsed light 831) and probe light 932 respectively irradiate the electromagnetic wave generating element 800 and the electromagnetic wave detection element 940 through lenses 990 and 980 as optical units. In this example, a 1.5-μm wavelength fiber femtosecond laser was used as the excited laser light source 830. The element 800 is the terahertz wave generating element according to the present invention and it configures a terahertz wave generating device in which the pump light having passed through the lens irradiates an optical irradiation surface of an electrode gap. A generated terahertz wave is guided by terahertz wave guides 933 and 935 into a specimen 950. The terahertz wave containing information on absorption spectrum of the specimen 950 is detected by the electromagnetic wave detection element 940 via terahertz wave guides 934 and 936. In this case, the electromagnetic wave detection element 940 uses a conventional LT-GaAs-based photoconductive element, and the value of a detection current of an ammeter 960 is proportional to the amplitude of the terahertz wave. Since GaAs was used on the detection side, a second harmonic generator (SHG crystal) 970 was inserted on the probe light 932 side. To perform time-resolved measurement, for example, the optical delay system 920 for varying the optical path length on the probe light 932 side is moved so as to control irradiation timings of the pump light and the probe light. Note that, the photoconductive element according to the present invention may also be used on the detection side to configure a system in which no SHG crystal is needed.

As described above, the terahertz time domain spectroscopy apparatus includes: the terahertz wave generating device including the electromagnetic wave generating element; and the terahertz wave detection device including the electromagnetic wave detection element. Through the control of a time difference between the terahertz wave generation timing of the electromagnetic wave generating element and the terahertz wave detection timing of the electromagnetic wave detection element, a time waveform of the generated terahertz wave pulse is measured based on the principle of sampling. In this configuration, at least one of the terahertz wave generating device and the terahertz wave detection device can be constituted by the terahertz wave generating/detecting device of the present invention.

The driving conditions of the time domain spectroscopy apparatus are as follows. The electromagnetic wave generating element 800 according to the present invention is applied with a voltage of 20 V from a voltage source 820 and irradiated with ultrashort-pulsed light as the pump light 931 for 30 fsec at an average power of 20 mW. On the detection side, a detection current obtained by irradiation of the probe light 932 of 5 mW is converted into a voltage signal by a transimpedance amplifier having a gain of about $10^7$ and a bandwidth of 10 kHz, and which is filtered as necessary. Typically, a terahertz wave pulse with a peak around 100 mV is observed. Through the modulation of the optical path length on the probe side by the delay stage 920, a time waveform of the generated terahertz wave pulse can be measured based on the principle of sampling. After the obtained time waveform is subjected to Fourier transform, it is found that the bandwidth exceeding 5 THz can be obtained. Those driving conditions are an example, and the voltage and the irradiation light power are not limited to the above-mentioned values. Alternatively, the application voltage of the electromagnetic wave generating element may be modulated at 10 kHz or the light intensity may be modulated by an optical chopper to detect a signal by a lock-in amplifier. In this way, a terahertz time domain spectroscope system can be constituted by at least one terahertz wave generating/detecting device of the present invention.

EXAMPLE 2

Example 2 of the first embodiment is described. In this example, in order to more improve the resistivity, the In composition of the semiconductor low temperature growth layer 14 was set to 0.45. Although the band gap wavelength is 1.49 µm, since an electric field is applied for the function as a generating element, actually, laser light in the vicinity of 1.55 µm can also be absorbed.

In this case, the InGaAs layer 11 was set to have a total thickness of 270 nm, in which the thickness of a lattice-matched layer having an In composition of 0.53 was 250 nm and the thickness of a graded layer for reducing the In composition from 0.53 to 0.45 was 20 nm. The InAlAs layer 12 was 20 nm thick having an In composition of 0.45 (lattice constant: 0.584 nm). The InGaAs layer 13 was 5 nm thick having an In composition of 0.45 (lattice constant: 0.584 nm). Note that, the lattice constant values were determined according to the Vegard's law. In this case, the degree of lattice mismatch with the InP substrate exceeds 0.5%. It follows that the InAlAs layer 12 and the InGaAs layer 13, which are semiconductor layers, are not lattice-matched with the substrate. On the other hand, the InAlAs layer 12 and the InGaAs layer 13, which are semiconductor layers, are lattice-matched with the semiconductor low temperature growth layer 14. In other words, the semiconductor low temperature growth layer 14 used in Example 2 includes a semiconductor that lattice-matches with the semiconductor layers but does not lattice-match with the InP substrate which is a semiconductor substrate.

The InGaAs layer 11 as one of the semiconductor layers includes a first semiconductor region and a second semiconductor region. The second semiconductor region is a lattice-matched layer having an In composition of 0.53 and therefore it includes a semiconductor that lattice-matches with the semiconductor substrate. The first semiconductor region is a graded layer for reducing the In composition from 0.53 to 0.45 and therefore includes a semiconductor that lattice-matches with the semiconductor low temperature growth layer in part having an In composition of 0.45. This reduction in In composition increases the energy band gap to increase the resistance so that the application voltage can be increased. The terahertz wave generation efficiency can thus be improved. For use as a detector, a dark current can be reduced to thereby noise is also reduced. As described above, in this example, the semiconductor low temperature growth layer includes a semiconductor that does not lattice-match with a semiconductor substrate used for growth, and the semiconductor growth layers grown at a normal temperature each include a semiconductor that lattice-matches with the semiconductor substrate used for growth.

EXAMPLE 3

Figure 7:
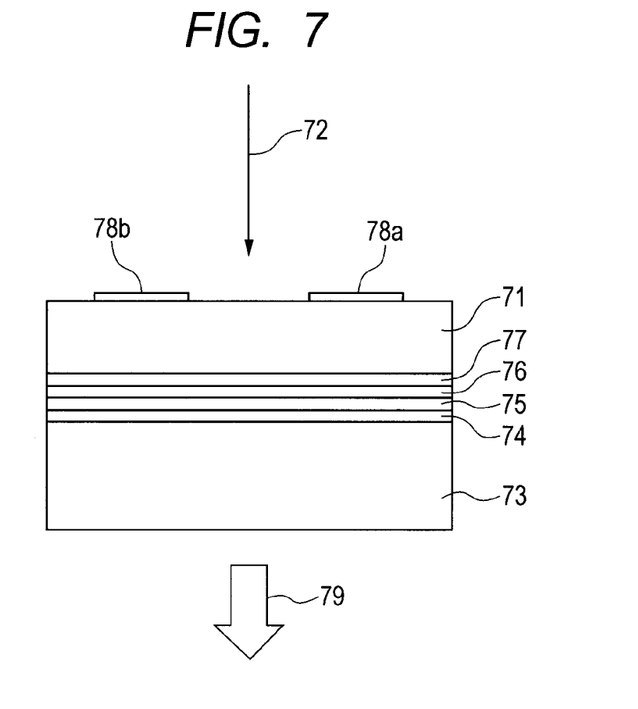
FIG. 7 is another cross-sectional structural diagram of the photoconductive element according to the first embodiment of the present invention.

Example 3 of the first embodiment is described with reference to FIG. 7. In this example, in order to more improve the resistivity, LT-GaAs is used for a semiconductor low temperature growth layer 71. Although the band gap wavelength of GaAs is about 0.87 µm, it is known that laser light 72 at a wavelength of 1.55 µm can also be absorbed through a two-stage absorption process or a two-photon absorption process using an intermediate level in the band gap (Applied Physics Letters, vol. 77, p. 1396 (2000)). This is a practical method in the case where the laser light 72 has high peak power for mainly utilizing a non-linear process. It is therefore effective to reduce the pulse width of the laser light 72 to enhance peak power. Alternatively, the peak power may be enhanced by reducing a focused beam diameter (1/e^2) of the laser light 72 on the semiconductor low temperature growth layer 71.

In the case where laser light 72 having a pulse width of 30 fs and a repetition frequency of 50 MHz is used and the beam diameter is set to 10 µm, the average power of the laser light 72 is typically set to 1 mW or more, desirably 10 mW or more. Of course, the settings are not limited to those values. For example, in the case where laser light 72 having a pulse width of 100 fs is used, the beam diameter may be more reduced or the average power may be more enhanced.

The intermediate level in the band gap depends mainly on As defects. In order to improve the number of excited carriers, it is desired to use semiconductor low temperature grown GaAs having a large number of As defects. In this example, LT-GaAs which is subjected to MBE growth at 250° C. is used.

As a substrate 73, SI-GaAs having a thickness of 500 µm is used. Between the semiconductor low temperature growth layer 71 and the substrate 73, respective semiconductor layers grown at a normal growth temperature (400° C. to 700° C.), namely an AlGaAs layer 77 (thickness: 50 nm, Al composition: 12%), an AlGaAs-graded layer 76 (thickness: 20 nm, Al composition: 100%→12%), an AlAs layer 75 (thickness: 100 nm), and an AlGaAs-graded layer 74 (thickness: 20 nm, Al composition 12%→100%), are formed. This configuration prevents the reduction in resistivity caused by an interface defect which occurs when the semiconductor low temperature growth layer 71 and the substrate 73 are formed in contact with each other. Further, the AlAs layer 75 having high resistance is sandwiched to reduce leakage of current into the substrate 73. The lattice constants of the respective materials are 0.5653 nm for GaAs, 0.5654 nm for AlGaAs (Al composition: 12%), and 0.5661 nm for AlAs (Semiconductors—Basic Data 2nd revised Edition (Otfried Madelung ed., Springer)). The degree of lattice mismatch is 0.1% or less between the respective layers.

On an upper portion of the semiconductor low temperature growth layer 71, antenna-electrodes 78a and 78b are formed.

In the case where the element of this example is used as a terahertz wave pulse generating element, a voltage is applied between the antenna-electrodes 78a and 78b. Through irradiation of the laser light 72 to a gap portion of the antenna-electrodes 78a and 78b, a terahertz wave 79 can be generated. In the case where the element of this example is used as a terahertz wave pulse detection element, the laser light 72 and the terahertz wave 79 are simultaneously irradiated to the gap portion of the antenna-electrodes 78a and 78b, and a current flowing between the antenna-electrodes 78a and 78b is detected.

An example of configuring a time domain spectroscopy apparatus by using the element of this example as a terahertz wave pulse generating element and a terahertz wave pulse detection element is as follows. Hereinafter, the difference from Example 1 is described. A schematic diagram of this example corresponds to that of FIG. 6 of Example 1 except that the second harmonic generator (SHG crystal) 970 is removed.

Each of the terahertz wave pulse generating element 800 and the terahertz wave pulse detection element 940 is an element in which LT-GaAs described in this example is used as the semiconductor low temperature growth layer 71. Also with LT-GaAs, carriers can be generated by the laser light 72 at a wavelength of 1.55 µm through the above-mentioned two-stage absorption process or two-photon absorption process. Therefore, a THz-TDS can be constituted without using the second harmonic generator (SHG crystal) 970 which is used in Example 1 (FIG. 6).

A gap distance between the antenna-electrodes 78a and 78b is 6 µm, and the lateral width of the gap is 10 µm. In this example, the diameter (1/e^2) of the laser light 72 on the gap is set to 10 µm, but it may be set to be smaller in order to enhance the power density of the laser light 72. Since the carriers are generated through a non-linear process, the increase in power density of the laser light on the gap can improve conversion efficiency of the laser light 72 into a terahertz wave. An excessively high power density, on the other hand, results in a saturation of the conversion efficiency, which is known in a normal photoconductive element. If a saturation phenomenon occurs, the frequency of a terahertz wave generally shifts to the low frequency side. In this case, it is necessary to select the laser diameter depending on a conversion efficiency or a frequency intended by a user.

The driving conditions of the time domain spectroscopy apparatus are as follows. The electromagnetic wave generating element 800 according to this example is applied with a sine wave voltage of 100 V (peak to peak) at a frequency of 50 kHz from the voltage source 820 and irradiated with ultrashort-pulsed light having a pulse width of 30 fsec and an average power of 30 mW as the pump light 931. The detection side is irradiated with the probe light 932 having an average power of 36 mW to generate a detection current.

Figure 8:
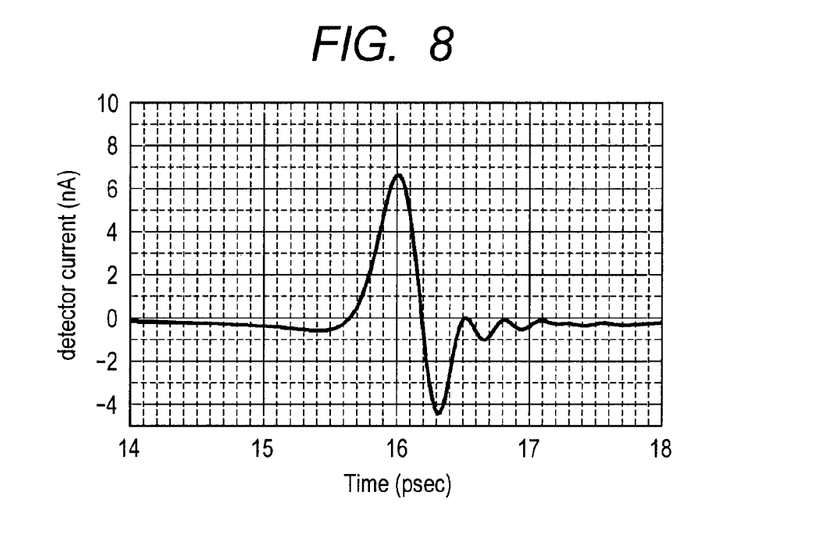
FIG. 8 illustrates a time waveform of a terahertz wave obtained in a spectroscopy apparatus according to the first embodiment of the present invention.

FIG. 8 illustrates a time waveform of a terahertz wave obtained by the THz-TDS described above. It is found that a pulse having a pulse with (full width at half maximum of electric field intensity) of about 300 fs is obtained.

Those driving conditions are an example, and the voltage and the irradiation light power are not limited to the above-mentioned values. Further, the element described in this example may be used as any one of the generating element 800 and the detection element 940. In this way, a terahertz time domain spectroscope system can be constituted by at least one terahertz wave generating/detecting device of the present invention.

EXAMPLE 4

Figure 9:
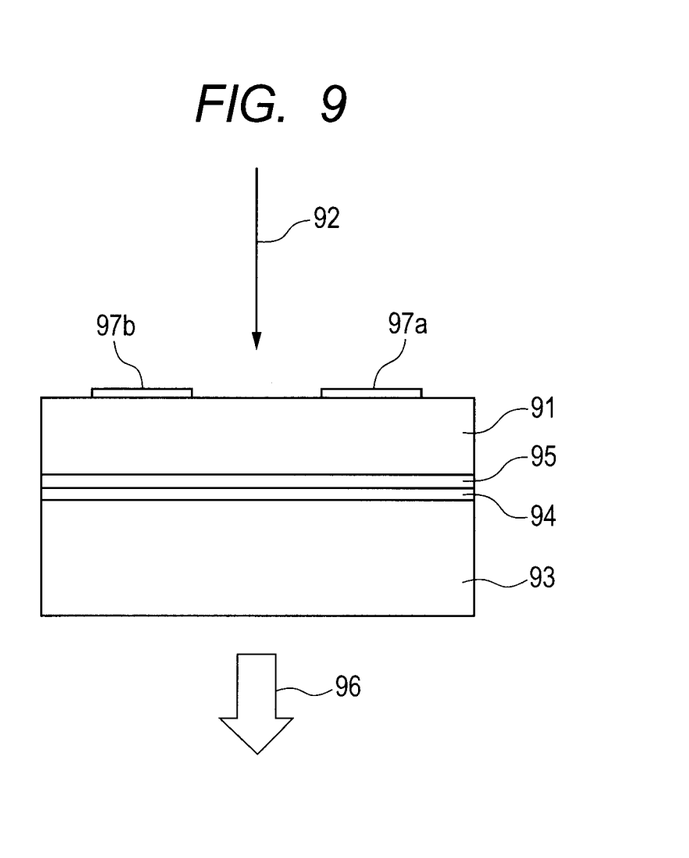
FIG. 9 is still another cross-sectional structural diagram of the photoconductive element according to the first embodiment of the present invention.

Example 4 of the first embodiment is described with reference to FIG. 9. This example uses LT-GaAs as a semiconductor low temperature growth layer 91 and Si as a substrate 93. A so-called high resistance Si is used for the Si substrate 93, and the resistivity of which is desirably 1 kohm·cm or more. Although a GaAs substrate is generally used for growth of a GaAs layer, the use of a Si substrate as exemplified in this example can reduce an absorption loss of a terahertz wave.

In this example, the Si substrate 93 having a thickness of 675 μm and a resistivity of 3 kohm·cm is used. The plane direction of the Si substrate 93 is set as a (100) surface and the off-angle is set to 6° toward <100>.

On the Si substrate 93, a Ge layer being a semiconductor layer is interposed as a buffer layer 94. On the buffer layer 94, an AlAs semiconductor layer is interposed as a carrier blocking layer 95. The buffer layer 94 and the carrier blocking layer 95 are grown at the above-mentioned normal growth temperature. For the growth, various methods including CVD and MBE may be used. The growth may be suspended between layers, such as between the buffer layer 94 and the carrier blocking layer 95. Alternatively, the respective layers may be grown in different apparatus. The lattice constants of the respective materials are 0.5653 nm for GaAs, 0.5431 nm for Si, 0.5658 nm for Ge, and 0.5661 nm for AlAs (Semiconductors—Basic Data 2nd revised Edition (Otfried Madelung ed., Springer)). The degree of lattice mismatch is 4.09% between Si and GaAs (lattice mismatch), 4.18% between Si and Ge (lattice mismatch), and 0.08% between Ge and GaAs (lattice match). Although the lattice constants of the Si substrate 93 and the LT-GaAs semiconductor low temperature growth layer 91 are greatly different, the lattice constant difference can be absorbed by the buffer layer 94, and hence the LT-GaAs semiconductor low temperature growth layer 91 can be grown with good crystallinity. In order to reduce the absorption of a terahertz wave 96, it is desired that the buffer layer 94 be as thin as possible in a range that does not deteriorates the crystallinity of the semiconductor low temperature growth layer 91. The thickness is desirably 1 μm or less. The carrier blocking layer 95 is provided for preventing a current path from being formed to the buffer layer 94 having low resistivity, and a higher resistive material than that of the buffer layer 94 is used for the carrier blocking layer 95. The resistivity is desirably 10^8 ohm·cm or more. In this example, the thickness of the carrier blocking layer 95 is 1 μm. The carrier blocking layer 95 may be multi-layered as illustrated in FIG. 7, or alternatively, a graded layer may be interposed therein.

The thickness of the LT-GaAs semiconductor low temperature growth layer 91 is 1.5 μm. As the thickness increases, the absorption amount of laser light 92 increases, which increases, however, the risk that the thickness approaches a critical thickness and the crystallinity deteriorates. The growth temperature of the LT-GaAs semiconductor low temperature growth layer 91 is 250° C.

Antenna-electrodes 97a and 97b are provided in contact with the semiconductor low temperature growth layer 91. Through irradiation of the laser light 92 to a gap between the antenna-electrodes 97a and 97b under the application of voltage, a terahertz wave 96 is generated. Although the generated terahertz wave 96 is irradiated to the space through the substrate 93 and the like, the use of high resistance Si as the substrate 93 as exemplified in this example reduces an absorption loss of the terahertz wave 96.

The above-mentioned physical properties of the respective layers, including the thickness, the material, and the resistivity, are an example, and are not limited to the values described above. For example, depending on the wavelength of the laser light 92, $In_xGa_{1-x}As$ ($0 \leq x \leq 1$), $GaAs_ySb_{1-y}$ ($0 \leq y \leq 1$), or the like may be used for the semiconductor low temperature growth layer 91.

With the use of the element described in this example, a generating element or a detection element capable of reducing an absorption loss of a terahertz wave by a substrate can be provided.

Note that, the thickness, the composition, and the material described in Examples 1, 2, 3, and 4 are an example. The effects of the present invention (improvement of characteristics of semiconductor low temperature growth layer) can be obtained when the normal temperature growth layers and the semiconductor low temperature growth layer exhibiting the functions described in the first embodiment are used in combination.

(Second Embodiment)

Figure 2:
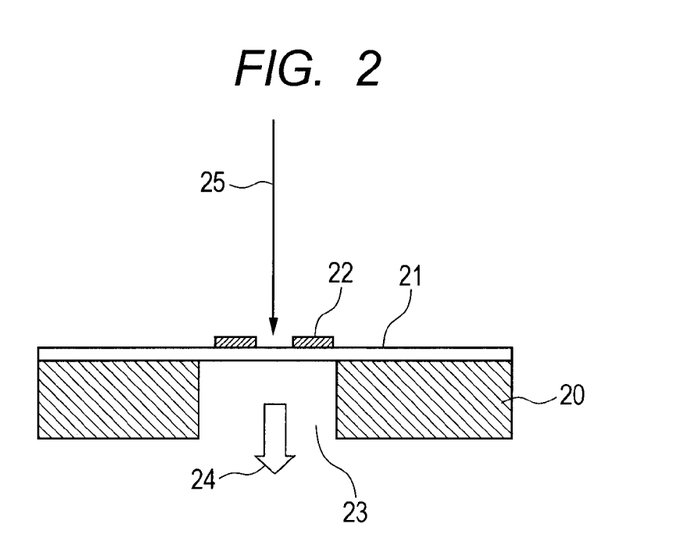
FIG. 2 is a cross-sectional structural diagram of a photoconductive element according to a second embodiment of the present invention.

In a second embodiment of the present invention, as illustrated in FIG. 2, a hole 23 is opened in part of a support substrate 20. The reason is that the hole 23 allows a terahertz wave 24, which is generated through irradiation of excited laser light 25 to a gap portion of antenna-electrodes 22 on a semiconductor layer 21, to be directly emitted instead of transmitting through the substrate 20. In this embodiment, the semiconductor layer 21 is a multi-layered semiconductor layer described in the first embodiment. On this occasion, in the conventional case where only a semiconductor low temperature growth layer is formed, a thin film portion having a hole opened therein is vulnerable to breakage. However, if the normal temperature growth layer is interposed as in the present invention, the strength can be improved. In this embodiment, the substrate 20 used for epitaxial growth of the semiconductor layer 21 is used without any processing. Alternatively, the formation of a hole may be applied to such a form that the semiconductor layer 21 is transferred to another substrate as described in later in a third embodiment of the present invention.

In hole processing, an etching stop layer may be provided between the semiconductor substrate and the semiconductor layer to improve the controllability. For example, for an InP system, InGaAs (layer 11 of FIG. 1) described in the first embodiment is used as an etching stop layer. In this embodiment, excited light and a generated terahertz wave both propagate through a vacuum or air and propagation through a substance is lessened. Consequently, a terahertz wave in a wide bandwidth can be generated with little influence of wavelength dispersion of materials.

(Third Embodiment)

In the third embodiment of the present invention, a difference from the first and second embodiments is that a photoconductive element is formed in a manner that a semiconductor layer is transferred onto a support substrate which is different from the substrate used for epitaxial growth of the semiconductor layer or another structure. In general, a compound semiconductor substrate such as InP and GaAs has a phonon absorption band in the vicinity of 7 THz in which a generated terahertz wave is absorbed. This is responsible for bandwidth limitation. To avoid this, it is conceivable to open a hole in the substrate as in the second embodiment, but, in this embodiment, the semiconductor layer is transferred onto a Si substrate or the like. In other words, this embodiment has the feature that a configuration including semiconductor normal temperature growth layers, a semiconductor low temperature growth layer, and electrodes is bonded onto a substrate which is different from a semiconductor substrate used for growth thereof. As the method of reducing the absorption by a substrate, epitaxial growth of a low temperature growth layer on a Si substrate as described in Example 4 of the first embodiment can be conceivable. Another conceivable method for realizing the reduction of absorption is used in this embodiment.

Figure 3A:
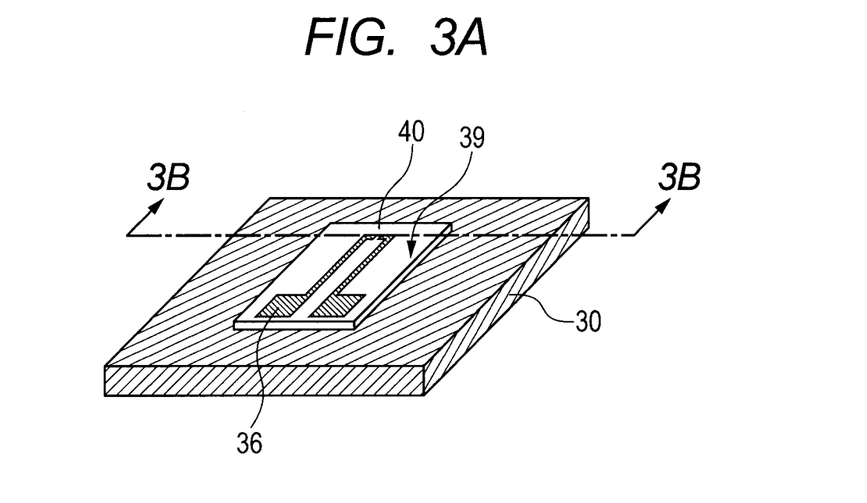
FIGS. 3A and 3B are a bird's eye view and a cross-sectional structural diagram, respectively, of a photoconductive element according to a third embodiment of the present invention.
Figure 3B:
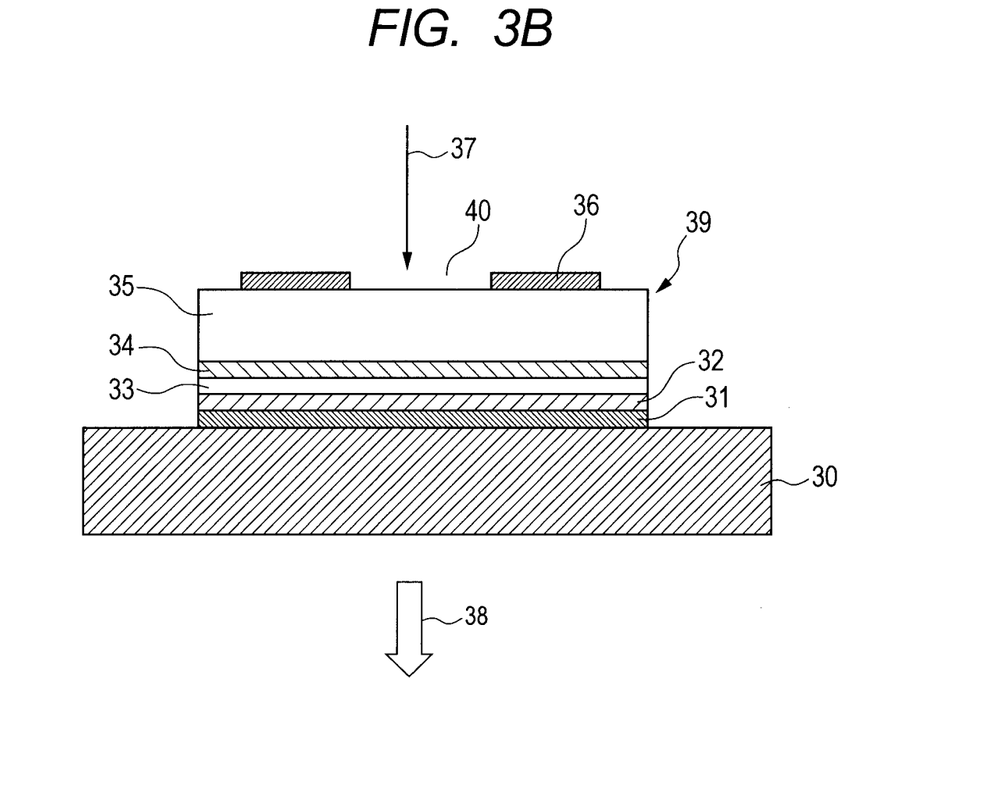

FIG. 3A is a bird's eye view illustrating this state and FIG. 3B is a cross-sectional diagram taken along the line 3B-3B of FIG. 3A. For example, in the case of a photoconductive element made of LT-InGaAs as exemplified in the first embodiment, an InGaAs layer 32, an InAlAs layer 33, and an InGaAs layer 34 are grown on an InP substrate at a normal growth temperature. An InGaAs layer 35 is then formed by low temperature growth as a semiconductor low temperature growth layer, and a pair of electrodes 36 is formed. After that, the opposite side to the substrate is bonded to a glass substrate or the like and the InP substrate is removed. Then, the epitaxial layer 39 is bonded onto a high resistance Si substrate 30 via an adhesive layer 31. In this case, an epoxy resin or the like may be used as the adhesive layer 31, of which thickness is typically about 10 µm, desirably 5 µm or less in order to avoid a loss or multireflection. As the Si substrate 30, a substrate having a resistivity of 10 kohm·cm or more is suitably used. After that, the glass substrate (not shown) is removed, to thereby obtain the form illustrated in FIGS. 3A and 3B.

Figure 4:
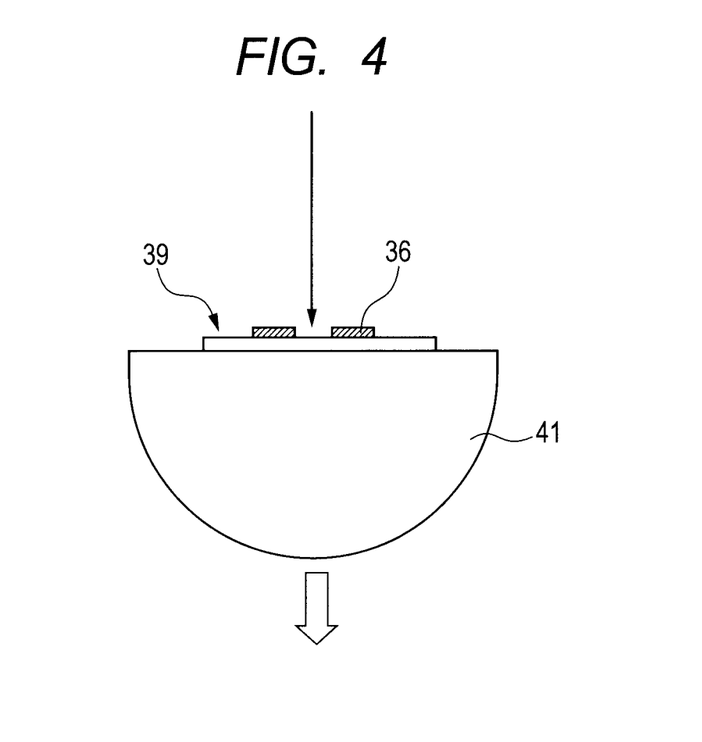
FIG. 4 is another cross-sectional structural diagram of the photoconductive element according to the third embodiment of the present invention.

In this case, when laser light 37 irradiates a gap portion 40 of the pair of electrodes 36 and a voltage is applied between the electrodes 36, a terahertz wave 38 is generated without being affected by phonon absorption of the substrate. The photoconductive element may also be used as a detector in which no voltage is applied and a terahertz wave is incident in the opposite direction to the direction of the terahertz wave 38. Other than the Si substrate 30, a substrate having a small terahertz wave loss, as exemplified by a quartz substrate and a resin substrate, can be used. Instead of using a flat substrate, as illustrated in FIG. 4, the epitaxial layer 39 may be directly bonded onto a hemispherical Si lens 41 so as to improve extraction efficiency of a terahertz wave.

In this embodiment, the normal temperature growth layers are present when the semiconductor layer is transferred, and hence it is possible to prevent the breakage caused by distortions and defects of the epitaxial layer 39 when the substrate is removed. This is particularly effective when the degree of lattice mismatch becomes larger for increasing the band gap. Note that, the heterojunction InAlAs layer 33 may be reinforced so that the InGaAs layer 32 may be removed after the removal of the InP substrate.

(Fourth Embodiment)

Figure 5:
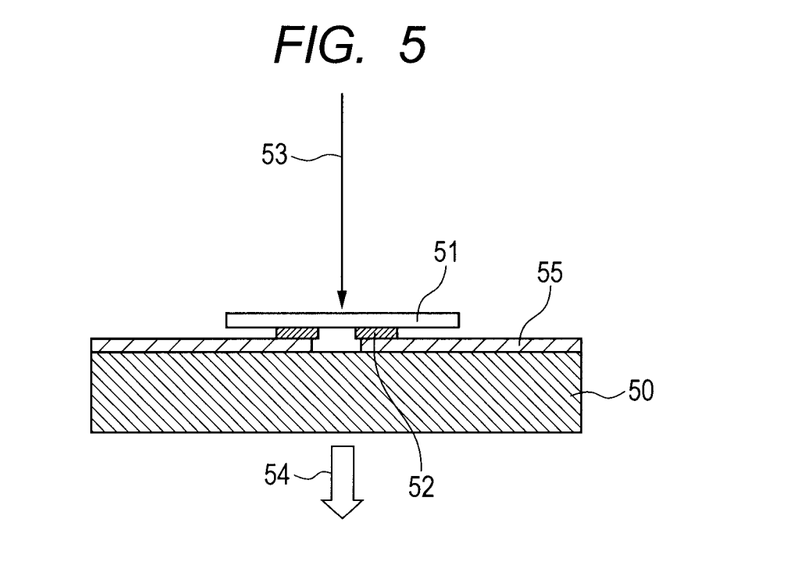
FIG. 5 is a cross-sectional structural diagram of a photoconductive element according to a fourth embodiment of the present invention.

A fourth embodiment of the present invention is described. In this embodiment, as illustrated in FIG. 5, an electrode-antenna 52 side is bonded onto a support substrate 50, and a semiconductor layer 51 is transferred onto the support substrate 50 while a semiconductor substrate used for epitaxial growth is removed. Electrode wiring 55 for biasing is formed in advance on the surface of the substrate 50 and it is bonded so that the electrodes on the surface of the semiconductor layer 51 are electrically connected to each other. In this structure, as the support substrate 50, high-resistivity silicon, quartz, and resin such as olefin, teflon, and polyethylene, which have good terahertz wave transparency, can be suitably used.

Excited laser light 53 enters from the side of the semiconductor layer 51 on which the electrodes 52 are not provided, and a terahertz wave pulse 54 is generated and emitted based on the same principle as in the first embodiment. The support substrate 50 may be formed into a lens shape or provided with an additional lens in order to improve the directivity of terahertz wave irradiation. In the fourth embodiment, the excited light irradiates the semiconductor layer 51 from the side without the electrodes, and hence the excited light is not blocked by the electrodes irrespective of the beam diameter size. Irradiation efficiency of the excited light can thus be improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-061439, filed Mar. 18, 2011, which is hereby incorporated by reference herein in its entirety.

What is claimed is:

1. A photoconductive element, comprising:
   a semiconductor substrate;
   a semiconductor low temperature growth layer;
   electrodes provided on the low temperature growth layer; and
   a semiconductor layer, which is positioned between the semiconductor low temperature growth layer and the semiconductor substrate and which is thinner than the semiconductor low temperature growth layer,
   wherein the semiconductor layer is a layer grown at a growth temperature of 400° C. or more and 700° C. or less, and the semiconductor layer includes a first layer and a second layer,
   wherein the semiconductor low temperature growth layer includes a semiconductor which lattice-matches with the semiconductor layer and does not lattice-match with the semiconductor substrate, and
   wherein the first layer is in contact with the semiconductor low temperature growth layer, the first layer includes a semiconductor which lattice-matches with the semiconductor low temperature growth layer and does not lattice-match with the semiconductor substrate, the second layer is positioned between the first layer and the semiconductor substrate, the second layer includes a semiconductor which lattice-matches with the semiconductor low temperature growth layer and does not lattice-match with the semiconductor substrate, and the semiconductor in the first layer is different from the semiconductor in the second layer.

2. The photoconductive element according to claim 1, wherein the semiconductor layer has a band gap wider than a band gap of the semiconductor low temperature growth layer.

3. The photoconductive element according to claim 1, wherein the second layer is in contact with the semiconductor substrate.

4. The photoconductive element according to claim 3, wherein the first layer is in contact with the second layer, and the first layer includes a semiconductor with lattice constant different from the lattice constant of the second layer.

5. The photoconductive element according to claim 1, wherein a configuration including the semiconductor layer, the semiconductor low temperature growth layer, and the electrodes is formed on a second semiconductor substrate different from the semiconductor substrate, and then the second semiconductor substrate is removed.

6. The photoconductive element according to claim 1, wherein the semiconductor substrate includes a hole formed therein in part.

7. The photoconductive element according to claim 1, wherein the semiconductor low temperature growth layer comprises one of an $In_xGa_{1-x}As$ (0 <x <1) layer and a $GaAs_ySb_{1-y}$ (0<y<1) layer.

8. The photoconductive element according to claim 1, wherein the second layer is a layer including Ge.

9. A terahertz wave generating/detecting device, comprising:
   the photoconductive element according to claim 1;
   a light source for emitting light for exciting the photoconductive element; and
   an optical unit for irradiating an optical irradiation surface of the photoconductive element with the light of the light source.

10. A terahertz time domain spectroscopy apparatus, comprising:
    a terahertz wave generating device comprising an electromagnetic wave generating element; and
    a terahertz wave detection device comprising an electromagnetic wave detection element, the terahertz time domain spectroscopy apparatus being configured to measure, through control of a time difference between a terahertz wave generation timing of the electromagnetic wave generating element and
    a terahertz wave detection timing of the electromagnetic wave detection element, a time waveform of a generated terahertz wave pulse based on a principle of sampling,
    wherein at least one of the terahertz wave generating device and the terahertz wave detection device comprises the terahertz wave generating/detecting device according to claim 9.

11. The photoconductive element according to claim 1, wherein the semiconductor layer includes no compositionally graded layer.

12. A method of manufacturing a photoconductive element including a semiconductor low temperature growth layer, the method comprising:
    forming a semiconductor layer on a semiconductor substrate at a growth temperature of 400° C. or more and 700° C. or less; and
    forming the semiconductor low temperature growth layer on the semiconductor layer at a growth temperature of 200° C. or more and less than 400° C., the semiconductor low temperature growth layer including a semiconductor which lattice-matches with the semiconductor layer and does not lattice-match with the semiconductor substrate,
    wherein the semiconductor layer includes a first layer and a second layer, and
    wherein the first layer is in contact with the semiconductor low temperature growth layer, the first layer includes a semiconductor which lattice-matches with the semiconductor low temperature growth layer and does not lattice-match with the semiconductor substrate, the second layer is positioned between the first layer and the semiconductor substrate, the second layer includes a semiconductor which lattice-matches with the semiconductor low temperature growth layer and does not lattice-match with the semiconductor substrate, and the semiconductor in the first layer is different from the semiconductor in the second layer.

13. A photoconductive element, comprising:
    a semiconductor substrate;
    a semiconductor low temperature growth layer;
    electrodes provided on the low temperature growth layer; and
    a semiconductor layer, which is positioned between the semiconductor low temperature growth layer and the semiconductor substrate and which is thinner than the semiconductor low temperature growth layer,
    wherein the semiconductor low temperature growth layer includes a semiconductor which lattice-matches with the semiconductor layer and does not lattice-match with the semiconductor substrate,
    wherein the semiconductor layer includes a first layer and a second layer, the semiconductor substrate comprises a Si substrate, the semiconductor low temperature growth layer comprises a GaAs layer grown at a growth temperature of 200° C. or more and 400° C. or less, the first layer comprises a layer including As grown at a growth temperature of 400° C. or more and 700° C. or less, and the second layer comprises a layer including Ge grown at a growth temperature of 400° C. or more and 700° C. or less.

14. A method of manufacturing a photoconductive element including a semiconductor low temperature growth layer, the method comprising:
    forming a semiconductor layer on a semiconductor substrate at a growth temperature of 400° C. or more and 700° C. or less; and
    forming the semiconductor low temperature growth layer on the semiconductor layer at a growth temperature of 200° C. or more and less than 400° C., the semiconductor low temperature growth layer including a semiconductor which lattice-matches with the semiconductor layer and does not lattice-match with the semiconductor substrate,
    wherein the semiconductor layer includes a first layer and a second layer, the semiconductor substrate comprises a Si substrate, the semiconductor low temperature growth layer comprises a GaAs layer grown at a growth temperature of 200° C. or more and 400° C. or less, the first layer comprises a layer including As grown at a growth temperature of 400° C. or more and 700° C. or less, and the second layer comprises a layer including Ge grown at a growth temperature of 400° C. or more and 700° C. or less.

* * * * *